United States Patent
Consoli et al.

(10) Patent No.: US 11,285,091 B2
(45) Date of Patent: Mar. 29, 2022

(54) M-AMINOPHENOL-FREE HAIR-COLOURING COMPOSITIONS

(71) Applicant: BEAUTY & BUSINESS S.p.A., Milan (IT)

(72) Inventors: Antonio Consoli, Urgnano (IT); Katiuscia Grevalcuore, Bergamo (IT); Massimo Fabbi, Mozzo (IT); Emanuela Facchetti, Romano di Lombardia (IT)

(73) Assignee: BEAUTY & BUSINESS S.p.A., Milan (IT)

(*) Notice: Subject to any disclaimer, the term of this patent is extended or adjusted under 35 U.S.C. 154(b) by 0 days.

(21) Appl. No.: 17/114,815

(22) Filed: Dec. 8, 2020

(65) Prior Publication Data
US 2021/0177717 A1 Jun. 17, 2021

(30) Foreign Application Priority Data
Dec. 16, 2019 (IT) .................. 102019000024126

(51) Int. Cl.
| | |
|---|---|
| *A61Q 5/10* | (2006.01) |
| *A61K 8/41* | (2006.01) |
| *A61K 8/06* | (2006.01) |
| *A61K 8/19* | (2006.01) |
| *A61K 8/24* | (2006.01) |
| *A61K 8/34* | (2006.01) |
| *A61K 8/37* | (2006.01) |
| *A61K 8/42* | (2006.01) |
| *A61K 8/44* | (2006.01) |
| *A61K 8/49* | (2006.01) |
| *A61K 8/60* | (2006.01) |

(52) U.S. Cl.
CPC ............ *A61K 8/411* (2013.01); *A61K 8/06* (2013.01); *A61K 8/19* (2013.01); *A61K 8/24* (2013.01); *A61K 8/347* (2013.01); *A61K 8/37* (2013.01); *A61K 8/41* (2013.01); *A61K 8/416* (2013.01); *A61K 8/42* (2013.01); *A61K 8/44* (2013.01); *A61K 8/4946* (2013.01); *A61K 8/60* (2013.01); *A61Q 5/10* (2013.01); *A61K 2800/30* (2013.01); *A61K 2800/48* (2013.01)

(58) Field of Classification Search
CPC ........ A61Q 5/10; A61K 8/411; A61K 8/4926; A61K 8/41; A61K 8/416; A61K 8/37; A61K 2800/48; A61K 8/06; A61K 8/19; A61K 8/347; A61K 2800/30
USPC .......................................................... 8/405
See application file for complete search history.

(56) References Cited

U.S. PATENT DOCUMENTS

| | | | | |
|---|---|---|---|---|
| 8,529,637 | B2 * | 9/2013 | Vohra .................. | A61K 8/046 8/405 |
| 8,632,611 | B2 * | 1/2014 | Agostino .............. | A61K 8/731 8/405 |
| 2008/0052841 | A1 * | 3/2008 | Cohen .................. | A61K 8/46 8/407 |
| 2012/0180230 | A1 * | 7/2012 | Schmenger .......... | A61Q 5/08 8/405 |
| 2013/0340181 | A1 * | 12/2013 | Sutton .................. | A61K 8/38 8/410 |
| 2017/0105921 | A1 * | 4/2017 | Fabbi .................... | A61K 8/22 |
| 2017/0258692 | A1 * | 9/2017 | Consoli ................ | A61K 8/415 |
| 2017/0258695 | A1 * | 9/2017 | Consoli ................ | A61K 8/55 |

FOREIGN PATENT DOCUMENTS

| | | |
|---|---|---|
| CA | 2576189 A1 | 6/2007 |
| WO | 2001051019 A1 | 7/2001 |
| WO | 2015138576 A1 | 9/2015 |
| WO | 2016097229 A1 | 6/2016 |
| WO | 2018048933 A1 | 3/2018 |

OTHER PUBLICATIONS

Search Report and Written Opinion of priority application IT 201900024126 dated May 20, 2020.

* cited by examiner

*Primary Examiner* — Eisa B Elhilo
(74) *Attorney, Agent, or Firm* — Silvia Salvadori, P.C.; Silvia Salvadori

(57) ABSTRACT

Disclosed are m-aminophenol-free hair-colouring compositions comprising a mixture of dyes consisting of methoxymethyl-p-phenylenediamine, hydroxyethyl-3,4-methylenedioxyaniline and 5-amino-6-chloro-o-cresol, an alkalising agent, and optionally other oxidative dyes, provided that they are not p-phenylenediamine or p-toluenediamine
The compositions according to the invention provide stable colours that do not change with time.

8 Claims, No Drawings

M-AMINOPHENOL-FREE HAIR-COLOURING COMPOSITIONS

This U.S. Non-Provisional Application claims priority to and the benefit from Italian Patent Application No. 102019000024126 filed on Dec. 16, 2019, the content of which is incorporated by reference in its entirety.

The present invention relates to hair-colouring compositions comprising a mixture of oxidative dyes and not containing m-aminophenol.

PRIOR ART

Dyeing is one of the main cosmetic hair treatments. The main hair-dyeing methods are the semi-permanent system and the permanent oxidative system. The first involves the use of direct dyes which are deposited on the hair surface. With this system, the colour gradually fades every time the hair is shampooed, and eventually disappears within 10 washes.

With the permanent oxidative system, the colour is created by the reaction of primary intermediates and couplers in the presence of an oxidant, and the stability of the colour to washing ranges from four to eight weeks. The oxidative system is based on the reaction of primary intermediates and couplers, both of which are practically colourless. In the presence of air or oxidants such as hydrogen peroxide, primary dyes, which are typically primary aromatic amines with a hydroxyl or additional amino group, substituted or not substituted, in the para or ortho position, react with couplers such as resorcinol, m-aminophenol, m-phenylenediamine or 1-naphthol.

As the dye molecules thus formed in the cuticle are larger than the starting primary intermediates and highly diffusible couplers they remain trapped inside the hair, and for this reason no significant fading takes place as a result of successive washes or the action of external agents.

The primary dye which was historically most widely used to produce oxidative hair-colouring preparations was p-phenylenediamine (PPD), later replaced by p-toluenediamine (PTD), which is less inclined to cause sensitisation problems such as contact dermatitis or more serious allergic reactions, including anaphylactic shock. However, the use of PTD instead of PPD has introduced some drawbacks in terms of both formulation and performance.

PTD is mainly marketed in the form of the sulphate salt, which is more stable but difficult to use in systems that do not tolerate large percentages of salts, such as hair-colouring preparations in liquid or gel form. Moreover, the use of large doses of PTD in emulsions is problematic due to separation. Hair-colouring preparations containing PTD also produce a less bright colour result than that obtained with PPD.

DE19957282 describes 2-methoxymethyl-p-phenylenediamine (MBB) as a novel primary dye which can also be used in combination with other commonly used primary dyes, such as PPD or PTD.

Subsequently, even hair-colouring preparations containing PTD began to cause more and more frequent cases of sensitisation; MBB has therefore proved to be a useful alternative as it has a lower sensitising power than both PPD and PTD.

Opinion 1509/13 of the Scientific Committee on Consumer Safety (SCCS) entitled "Memorandum on hair dye chemical sensitisation" dated 26 Feb. 2013 lists the sensitising power values of various oxidative and direct dyes, classified as Extreme Sensitisers, Strong Sensitisers, Moderate Sensitisers, Insufficiently Tested Dyes, and Non-classifiable Dyes.

p-phenylenediamine is classified as an extreme sensitiser, with an EC3 value of 0.06%, while PTD is an extreme sensitiser with an EC3 of 0.31%.

2-methoxymethyl-p-phenylenediamine is classed as a moderate sensitiser with an EC3 value of 7.11%.

2-methoxymethyl-p-phenylenediamine is also usually marketed as free base, which makes it much more versatile, and also easily usable in liquid or gel hair-colouring preparations which are incompatible with high percentages of salts.

The Applicant has studied the MBB dye, conducting a systematic evaluation of the various dye combinations, and found that the combination of m-aminophenol (MAP) and MBB produces a colour result which is particularly unstable over time after application to the hair.

MAP is one of the couplers most widely used in hair-colouring preparations containing PPD and PTD because it gives, in combination with them, brownish-violet colours which are particularly useful to create natural gold and copper shades. It is equally useful in combination with MBB to create natural gold or copper shades which, however, are unstable over time, with significant variations in colour after exposure to light and heat, even without washing. In particular, a loss of the violet component and a consequent colour change to brownish-yellow has been observed.

There is therefore a need for a permanent oxidative dye containing MBB but not containing PPD or PTD, which gives the hair a colour that remains stable over time without unwanted colour changes.

DESCRIPTION OF THE INVENTION

It has now been discovered that by introducing into the formulations the combination of 2-methoxymethyl-p-phenylenediamine, hydroxyethyl-3,4-methylenedioxyaniline and 5-amino-6-chloro-o-cresol, stable colours are obtained which do not change over time.

The subject of the invention is therefore a hair-colouring composition not containing m-aminophenol which comprises a mixture of dyes consisting of methoxymethyl-p-phenylenediamine, hydroxyethyl-3,4-methylenedioxyaniline and 5-amino-6-chloro-o-cresol, an alkaliser, and optionally other oxidative dyes provided that they are not p-phenylenediamine or p-toluenediamine Each of the three dyes, namely methoxymethyl-p-phenylenediamine, hydroxyethyl-3,4-methylenedioxyaniline and 5-amino-6-chloro-o-cresol, can be present in the composition in a weight percentage ranging from 0.01 to 6% of the weight of the composition.

The compositions according to the invention, mixed at a suitable dilution with an activator, dye the hair permanently and stably, without unwanted colour changes.

"Activator" means hydrogen peroxide, carbamide peroxide, perborates and persulphates or peracids. The preferred compound is hydrogen peroxide. The amount can range from 0.1 to 50%.

The compositions according to the invention can optionally be in "ready-to-use" form, comprising two or more ingredients to be mixed before use. Depending on their composition, the ready-to-use hair-colouring preparations according to the invention can be weakly acidic, neutral or alkaline, and have a pH ranging from about 3 to 11, preferably from 6.5 to 11.

The composition comprises an alkalising agent selected, for example, from ammonia, monoethanolamine (MEA), 1-amino-2-propanol, 2-amino-2-methyl-propanol (AMP), 2-amino-2-methyl-1,3-propanediol, 2-amino-2-ethyl-1,3-propanediol and tris(hydroxymethyl)-aminomethane (tromethamine, Tris), sodium hydroxide, potassium hydroxide, urea, allantoin, arginine, tripotassium phosphate, sodium saccharine, triethanolamine (TEA) or combinations thereof.

The amount of alkalising agent can range between 0.1 and 20% by weight, preferably between 0.2 and 10% by weight.

The composition according to the invention can also contain other oxidative dyes in addition to the three cited above. The preferred dyes are listed below according to the INCI nomenclature (International Nomenclature of Cosmetic Ingredients):

1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulphate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-((4-Chlorophenyl)Methyl)-1H-Pyrazole-Sulphate, 2,3-Diaminodihydropyrazolo Pyrazolone Dimethosulphonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl-4,5-DiaminoPyrazole Sulphate, Hydroquinone, Hydroxyanthraquinone-aminopropyl Methyl Morpholinium Methosulphate, Hydroxybenzomorpholine, Hydroxyethoxy Aminopyrazolopyridine, Hydroxyethylaminomethyl-p-Aminophenol, 1-Hydroxyethyl 4,5-Diamino Pyrazole, Hydroxyethyl-2,6-Dinitro-p-Anisidine, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazolium-propyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, Phenyl Methyl Pyrazolone, N-Phenyl-p-Phenylenediamine, Picramic Acid, Pyrocatechol, Pyrogallol, Sodium Picramate, Tetraaminopyrimidine, Tetrahydro-6-Nitroquinoxaline, Tetrahydropyranyl, Resorcinol, Toluene-2,6-Diamine, Toluene-3,4-Diamine, 2,5,6-Triamino-4-Pyrimidinol, 1,2,4-Trihydroxybenzene.

Preferably, the compositions do not contain resorcinol or derivates thereof, such as 2-methyl-resorcinol or 4-chloro-resorcinol.

The oxidative dyes can be in the form of salts. The hair-colouring preparations according to the invention can also contain direct dyes. Examples of direct dyes, defined according to the INCI nomenclature (European Community Decision 2006/257/EC as amended—International Nomenclature of Cosmetic Ingredients), include:

Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

The hair-colouring preparations according to the invention can also contain one or more natural or synthetic additives commonly used in the cosmetics industry, such as solvents, surfactants, emulsifiers, wetting agents, thickeners, conditioners, etc.

Examples of solvents include water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monomethyl ether acetate or acetic acid hydroxyethyl ester; amides such as N-methylpyrrolidone; urea, tetramethyl urea and thiodiglycol.

The following can also be present: anionic, cationic, non-ionic, amphoteric or zwitterionic agents; wetting agents; surfactants, such as fatty alcohol sulphates, alkylsulphonates, alkylbenzene sulphonates, alklymethyl ammonium salts, alkylbetaine, α-olefin sulphonates, ethoxylated fatty alcohols, ethoxylated nonylphenols, fatty acid alkanolamines, ethoxylated esters of fatty acids, polyglycol ether sulphates of fatty acids and alkylpolyglycosides; thickeners, such as higher fatty alcohols, starches, cellulose derivatives, vaseline, paraffin oil, fatty acids and other fatty ingredients in emulsified form, water-soluble polymer thickeners, such as natural gums, guar gum, tara gum, xanthan gum, carob flour, pectin, dextran, agar-agar, amylose, amylopectin, dextrin, synthetic clays or hydrocolloids, such as polyvinyl alcohol; conditioning and restructuring agents such as lanolin derivatives, cholesterol, pantothenic acid, water-soluble cationic polymers, protein derivatives, amino acids, provitamins, vitamins, plant extracts, sugar and betaine; auxiliary agents such as electrolytes, antioxidants, fatty amides, sequestering agents, film-forming agents and preservatives, and beeswax.

The addition to the hair-colouring preparations according to the invention of non-ionic and/or anionic surfactants, such as fatty alcohol sulphates, in particular lauryl sulphate or sodium cocoyl sulphate; ethoxylated fatty alcohol sulphates, in particular sodium lauryl ether sulphates with 2 to 4 molecular units of ethylene oxide, ethoxylated esters of fatty acids, ethoxylated nonylphenols, ethoxylated fatty alcohols, alkylbenzene sulphonates or alkanolamides of fatty acids, in a total amount preferably ranging from about 0.1 to 30% by weight, more preferably from 0.2 to 15% by weight, can be particularly advantageous.

Examples of useful cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other useful cationic surfactants are quaternised protein hydrolysates.

As well as non-ionic organic thickeners with properties similar to wax and non-ionic surfactants, the hair-colouring preparation can include the usual cosmetic cationic resins. Polyquaternium 6, Polyquaternium-7, Polyquaternium-10, Polyquaternium-11, Polyquaternium-22, Polyquaternium-35, Polyquaternium-37 and Polyquaternium-113, either alone or mixtures thereof, are particularly preferred. The total amount of said additives in the preparation can range from about 0.1 to 6% by weight.

A preferred form of the invention involves the presence of ingredients alternative to silicones such as coco-caprylates, isododecane, C15-19 alkanes and isoamyl laurate.

Isoamyl laurate, an ingredient of 100% plant origin which is completely biodegradable, is particularly preferred, and included in the composition in an amount ranging from 0.01 to 10% of the weight of the composition.

The presence of isoamyl laurate not only gives the hair cosmetic properties (combability, shine) but also improves the fluidity of the mixture, making the mixture of dye and peroxide easier to apply.

Definitions

The International Colour Chart (ICC) is a system used to classify hair dyes. This means that every hair-colouring composition has a code defining its colour result. Said code can be used by manufacturers of colour charts or dyes. In practice, the ICC system uses numbers to define the depth (level) and tone of a given colour.

The colour "level" indicates how light or dark the shade is. The ICC (International Colour Chart) system uses numbers to define the depth of colour. Said values range from 1 to 11, wherein 1 denotes the darkest shade (black) and 11 the lightest shade (platinum blonde).

The usual level numbers and names are as shown in Table A

TABLE A

| Level | Level name |
|---|---|
| 1 | Black |
| 2 | Very dark brown |

TABLE A-continued

| Level | Level name |
|---|---|
| 3 | Dark brown |
| 4 | Medium brown |
| 5 | Light brown |
| 6 | Dark blonde |
| 7 | Medium blonde |
| 8 | Light blonde |
| 9 | Very light blonde |
| 10 | Lightest blonde |
| 11 | Platinum blonde |

The tone indicates how cool or warm a colour is, and includes colours such as gold, ash and copper.

Although the level measurement is almost identical for all manufacturers, each manufacturer follows its own system when classifying tone. Tone is indicated by a number, usually placed after the level, separated by a decimal point ".", a comma "," or a slash "/". The classification used by the Applicant is set out below:

| Tone number | Tone name |
|---|---|
| 0 | Natural (grey-neutral) |
| 1 | Ash (blue) |
| 2 | Irisé (violet) |
| 3 | Gold (yellow) |
| 4 | Copper (orange) |
| 5 | Mahogany (violet red) |
| 6 | Red (red) |
| 7 | Matte (green) |
| 8 | Pearl |

Some dyes can have a double tone, and it is usual to place two numbers after the decimal point of the level to express said characteristic. For example, if the colour chart contains the number 7.21, the first number indicates the medium blonde level (7), the second indicates the irisé tone (2), and the third number indicates a second ash tone (3). Said colour will be called "medium blonde irisé ash".

Examples

The ingredients listed in the examples are named according to the INCI nomenclature (European Community Decision 2006/257/EC as amended—International Nomenclature of Cosmetic Ingredients).

Table 1 shows the formulas of the activators used. Formulas A1, A2, A3 and A4 represent the different strengths of the activators, namely 40, 30, 20 and 10 volumes respectively.

TABLE 1

| | Activators | | | |
|---|---|---|---|---|
| INGREDIENTS | A1 % | A2 % | A3 % | A4 % |
| AQUA (WATER) | q.s. to 100 | q.s. to 100 | q.s. to 100 | q.s. to 100 |
| HYDROGEN PEROXIDE | 12 | 9 | 6 | 3 |
| CETEARYL ALCOHOL | 3 | 3 | 3 | 3 |
| CETEARETH-20 | 0.6 | 0.6 | 0.6 | 0.6 |
| PHOSPHORIC ACID | 0.1 | 0.1 | 0.1 | 0.1 |
| SODIUM STANNATE | 0.2 | 0.2 | 0.2 | 0.2 |
| SODIUM LAURETH SULPHATE | 0.1 | 0.1 | 0.1 | 0.1 |
| PROPYLENE GLYCOL | 0.5 | 0.5 | 0.5 | 0.5 |
| DISODIUM PYROPHOSPHATE | 0.1 | 0.1 | 0.1 | 0.1 |
| DIMETHICONE | 0.1 | 0.1 | 0.1 | 0.1 |

TABLE 1-continued

| | Activators | | | |
|---|---|---|---|---|
| INGREDIENTS | A1 % | A2 % | A3 % | A4 % |
| PEG-40 CASTOR OIL | 0.5 | 0.5 | 0.5 | 0.5 |
| PENTASODIUM PENTETATE | 0.1 | 0.1 | 0.1 | 0.1 |
| ETIDRONIC ACID | 0.1 | 0.1 | 0.1 | 0.1 |

Table 2 shows the compositions of the hair-colouring preparations in cream form used in the tests. Composition F1* is the composition according to the invention.

TABLE 2

| | Compositions in cream form | | | |
|---|---|---|---|---|
| | F1* | F2 | F3 | F4 |
| AQUA (WATER) | q.s. to 100 | q.s. to 100 | q.s. to 100 | q.s. to 100 |
| CETEARYL ALCOHOL | 20 | 20 | 20 | 20 |
| LAURETH-3 | 3 | 3 | 3 | 3 |
| SODIUM LAURETH SULPHATE | 1.65 | 1.65 | 1.65 | 1.65 |
| OLETH-5 PHOSPHATE | 1.02 | 1.02 | 1.02 | 1.02 |
| DIOLEYL PHOSPHATE | 0.98 | 0.98 | 0.98 | 0.98 |
| SODIUM LAURYL SULPHATE | 0.9 | 0.9 | 0.9 | 0.9 |
| GLYCERYL STEARATE SE | 0.75 | 0.75 | 0.75 | 0.75 |
| PARFUM (FRAGRANCE) | 0.6 | 0.6 | 0.6 | 0.6 |
| CERA ALBA (BEESWAX) | 0.5 | 0.5 | 0.5 | 0.5 |
| SODIUM SULPHATE | 0.5 | 0.5 | 0.5 | 0.5 |
| SODIUM SULPHITE | 0.5 | 0.5 | 0.5 | 0.5 |
| EDTA | 0.3 | 0.3 | 0.3 | 0.3 |
| ERYTHORBIC ACID | 0.2 | 0.2 | 0.2 | 0.2 |
| LIMNANTHES ALBA SEED OIL (LIMNANTHES ALBA (MEADOWFOAM) SEED OIL) | 0.2 | 0.2 | 0.2 | 0.2 |
| 2-METHYLRESORCINOL | — | — | — | 0.08 |
| TOLUENE-2,5-DIAMINE SULPHATE | — | — | — | 1.54 |
| 2,4-DIAMINOPHENOXYETHANOL HCl | 0.11 | 0.11 | 0.11 | 0.04 |
| 2-METHOXYMETHYL-P-PHENYLENEDIAMINE (MBB) | 2.52 | 2.52 | 2.52 | — |
| HYDROXYETHYL 3,4-METHYLENEDIOXYANILINE HCL | 3.35 | — | — | — |
| 5-AMINO-6-CHLORO-o-CRESOL | 0.11 | 0.11 | — | — |
| RESORCINOL | — | 1.7 | 1.7 | 0.55 |
| m-AMINOPHENOL | — | — | 0.08 | 0.014 |
| ETHANOLAMINE (MEA) | 1.1 | 1.1 | 1.1 | 1.1 |
| AMMONIA | 1.8 | 1.8 | 1.8 | 1.8 |

Test 1: Colour Change Due to Light and Heat

The test was conducted on IHIP level 10 Lightest Blonde locks of hair, which had been dyed with the formulations listed in Table 2 mixed with activator A2 at the ratio of 1:1.5, with a processing time of 35 minutes.

A Konica Minolta colorimeter was used to evaluate colour stability.

In the CIELAB colour space, $L^*$ indicates sheen and $a^*$ and $b^*$ are the colour coordinates. $a^*$ and $b^*$ indicate the colour directions: $+a^*$ is the direction of red, $-a^*$ is the direction of green, $+b^*$ is the direction of yellow and $-b^*$ is the direction of blue.

Parameter $b^*$ (direction of yellow) was considered for the example below. The higher parameter $b^*$, the greater the yellow component of the dye. If the yellow component increases, the violet component decreases. Violet is the component that changes most following exposure to light, air and heat of hair dyed with the dye pair MBB+MAP.

The locks were measured with the colorimeter at time 0 and after 60000 Kj of exposure to SUNTEST XLS+ (ATLAS) at the temperature of 50° C.

Table 3 shows the values of b* which represent the colour change of the different compositions over time.

TABLE 3

Colour change

|  | Δb* |
|---|---|
| F1* | 0.29 |
| F2 | 1.06 |
| F3 | 1.57 |
| F4 | 0.94 |

The data show that composition F3 containing the pair MBB and MAP exhibits a major colour change from violet to yellow. Composition F1* exhibits the smallest colour change after exposure to light and heat.

TABLE 4

Hair-colouring composition according to the invention in gel form, with resorcinol (resorcin).

| INGREDIENTS (INCI) | Composition F5* |
|---|---|
| AQUA | q.s. to 100 |
| PROPYLENE GLYCOL | 7 |
| HYDROXYETHYLCELLULOSE | 2 |
| CARBOMER | 1 |
| ACRYLATES/METHACRYLAMIDE COPOLYMER | 0.3 |
| SODIUM HYDROXIDE | 1 |
| PARFUM (FRAGRANCE) | 0.6 |
| SODIUM SULPHITE | 0.5 |
| ERYTHORBIC ACID | 0.3 |
| EDTA | 0.2 |
| 2-METHOXYMETHYL-P-PHENYLENEDIAMINE (MBB) | 2.8 |
| HYDROXYETHYL 3,4-METHYLENEDIOXYANILINE HCL (HMOC) | 0.1 |
| 5-AMINO-6-CHLORO-O-CRESOL | 0.13 |
| RESORCINOL | 1.25 |
| ETHANOLAMINE (MEA) | 1.1 |
| AMMONIA | 1.8 |
| ACID RED 92 | 0.1 |
| 1-HYDROXYETHYL 4,5-DIAMINO PYRAZOLE SULPHATE | 0.05 |

TABLE 5

Hair-colouring composition according to the invention in liquid form, without resorcinol or derivatives (without resorcins).

| | F6* |
|---|---|
| AQUA (WATER) | q.s. to 100 |
| ALCOHOL DENAT. | 12 |
| OLEIC ACID | 12 |
| PROPYLENE GLYCOL | 10 |
| LAURETH-2 | 8 |
| LAURETH-3 | 4 |
| OLEYL ALCOHOL | 3.5 |
| SODIUM LAURETH SULPHATE | 3 |
| POTASSIUM HYDROXIDE | 0.1 |
| PARFUM (FRAGRANCE) | 0.7 |
| CETRIMONIUM CHLORIDE | 0.5 |
| SODIUM SULPHITE | 0.5 |
| ERYTHORBIC ACID | 0.3 |
| EDTA | 0.2 |
| 2-METHOXYMETHYL-P-PHENYLENEDIAMINE (MBB) | 3 |
| HYDROXYETHYL - 3,4-METHYLENEDIOXYANILINE HCL | 0.4 |
| 5-AMINO-6-CHLORO-o-CRESOL | 0.6 |
| 2-AMINO-3-HYDROXYPYRIDINE | 1.8 |
| ETHANOLAMINE (MEA) | 1.1 |
| AMMONIA | 1.8 |
| 2-AMINO-6-CHLORO-4-NITROPHENOL | 0.5 |
| 1-HYDROXYETHYL 4,5-DIAMINO PYRAZOLE SULPHATE | 0.5 |

TABLE 6

Compositions in cream form according to the invention:

| | F7* | F8* | F9* | F10* | F11* | F12* | F13* |
|---|---|---|---|---|---|---|---|
| AQUA (WATER) | q.s. to 100 | q.s. to 100 | q.s. to 100 | q.s. to 100 | q.s. to 100 | q.s. to 100 | q.s. to 100 |
| CETEARYL ALCOHOL | 20 | 20 | 20 | 20 | 20 | 20 | 20 |
| LAURETH-3 | 3 | 3 | 3 | 3 | 3 | 3 | 3 |
| SODIUM LAURETH SULPHATE | 1.65 | 1.65 | 1.65 | 1.65 | 1.65 | 1.65 | 1.65 |
| OLETH-5 PHOSPHATE | 1.02 | 1.02 | 1.02 | 1.02 | 1.02 | 1.02 | 1.02 |
| DIOLEYL PHOSPHATE | 0.98 | 0.98 | 0.98 | 0.98 | 0.98 | 0.98 | 0.98 |
| SODIUM LAURYL SULPHATE | 0.9 | 0.9 | 0.9 | 0.9 | 0.9 | 0.9 | 0.9 |
| GLYCERYL STEARATE SE | 0.75 | 0.75 | 0.75 | 0.75 | 0.75 | 0.75 | 0.75 |
| PARFUM (FRAGRANCE) | 0.6 | 0.6 | 0.6 | 0.6 | 0.6 | 0.6 | 0.6 |
| CERA ALBA (BEESWAX) | 0.5 | 0.5 | 0.5 | 0.5 | 0.5 | 0.5 | 0.5 |
| SODIUM SULPHATE | 0.5 | 0.5 | 0.5 | 0.5 | 0.5 | 0.5 | 0.5 |
| SODIUM SULPHITE | 0.5 | 0.5 | 0.5 | 0.5 | 0.5 | 0.5 | 0.5 |
| EDTA | 0.3 | 0.3 | 0.3 | 0.3 | 0.3 | 0.3 | 0.3 |
| ERYTHORBIC ACID | 0.2 | 0.2 | 0.2 | 0.2 | 0.2 | 0.2 | 0.2 |
| LIMNANTHES ALBA SEED OIL (LIMNANTHES ALBA (MEADOWFOAM) SEED OIL) | 0.2 | 0.2 | 0.2 | 0.2 | 0.2 | 0.2 | 0.2 |

TABLE 6-continued

Compositions in cream form according to the invention:

| | F7* | F8* | F9* | F10* | F11* | F12* | F13* |
|---|---|---|---|---|---|---|---|
| p-METHYLAMINOPHENOL SULPHATE | 0.2 | — | — | — | — | — | — |
| 2-METHYLRESORCINOL | — | 0.3 | — | — | — | — | — |
| 4-CHLORORESORCINOL | — | — | 0.1 | — | — | — | — |
| 1-NAPHTHOL | — | — | — | 0.4 | — | — | — |
| 2-AMINO-3-HYDROXYPYRIDINE | — | — | — | — | 0.1 | — | — |
| 4-AMINO-2-HYDROXYTOLUENE | — | — | — | — | — | 0.6 | — |
| N,N-BIS(2-HYDROXYETHYL)-p-PHENYLENEDIAMINE SULPHATE | — | — | — | — | — | — | 0.2 |
| 2-AMINO-4-HYDROXYETHYLAMINO-ANISOLE SULPHATE | 0.1 | — | — | — | — | — | — |
| 4-AMINO-m-CRESOL | — | 0.3 | — | — | — | — | — |
| PHENYL METHYL PYRAZOLONE | — | — | 0.4 | — | — | — | — |
| 2,4-DIAMINOPHENOXYETHANOL HCl | — | — | — | 0.1 | — | — | — |
| 2-METHYL-5-HYDROXYETHYLAMINO-PHENOL | — | — | — | — | 0.6 | — | — |
| TBHQ | — | — | — | — | — | 0.1 | — |
| 1-HYDROXYETHYL 4,5-DIAMINO PYRAZOLE SULPHATE | — | — | — | — | — | — | 0.05 |
| TETRAAMINOPYRIMIDINE SULPHATE | 0.3 | — | — | — | — | — | — |
| 2,6-DIHYDROXYETHYLAMINO-TOLUENE | — | 0.15 | — | — | — | — | — |
| 2,6-DIAMINOPYRIDINE | — | — | 0.4 | — | — | — | — |
| p-AMINOPHENOL | — | — | — | 0.17 | — | — | — |
| HYDROXYETHYL-p-PHENYLENEDIAMINE SULPHATE | — | — | — | — | 0.22 | — | — |
| 6-METHOXY-2-METHYLAMINO-3-AMINOPYRIDINE HCL | — | — | — | — | — | 0.14 | — |
| 2,6-DIHYDROXY-3,4-DIMETHYLPYRIDINE | — | — | — | — | — | — | 0.08 |
| 2-METHOXYMETHYL-P-PHENYLENEDIAMINE (MBB) | 2.15 | 2.8 | 1.5 | 2.9 | 1.35 | 0.5 | 0.8 |
| HYDROXYETHYL 3,4-METHYLENEDIOXYANILINE HCL | 0.2 | 0.5 | 0.12 | 1.15 | 1.56 | 1.47 | 2.5 |
| 5-AMINO-6-CHLORO-o-CRESOL | 0.6 | 0.8 | 0.15 | 0.45 | 0.26 | 0.1 | 0.05 |
| RESORCINOL | — | 0.1 | — | — | — | 0.01 | — |
| ETHANOLAMINE (MEA) | 1.1 | 1.1 | 1.1 | 1.1 | 1.1 | 1.1 | 1.1 |
| AMMONIA | 1.8 | 1.8 | 1.8 | 1.8 | 1.8 | 1.8 | 1.8 |
| ISOAMYL LAURATE | 1 | — | 0.5 | — | — | 1 | — |

The invention claimed is:

1. m-aminophenol-free hair-colouring composition comprising methoxymethyl-p-phenylenediamine, hydroxyethyl-3,4-methylenedioxyaniline and 5-amino-6-chloro-o-cresol, an alkalising agent, and optionally other oxidative dyes, with the proviso that they are not p-phenylenediamine or p-toluenediamine.

2. A composition according to claim 1 further comprising one or more direct dyes.

3. A composition according to claim 1 wherein the optional other oxidative dyes do not include resorcinol or derivatives thereof.

4. A composition according to claim 1 wherein the alkalising agent is selected from ammonia, monoethanolamine, 1-amino-2-propanol, 2-amino-2-methyl-propanol, 2-amino-2-methyl-1,3-propanediol, 2-amino-2-ethyl-1,3-propanediol, tris (hydroxymethyl)-aminomethane, sodium hydroxide, potassium hydroxide, urea, allantoin, arginine, tripotassium phosphate, sodium saccharine, triethanolamine or combinations thereof, in amounts ranging from 0.1 to 20% by weight.

5. A composition according to claim 1 wherein methoxymethyl-p-phenylenediamine, hydroxyethyl-3,4-methylenedioxyaniline and 5-amino-6-chloro-o-cresol are each present in a weight percentage ranging from 0.01 to 6%.

6. A composition according to claim 1 further comprising solvents, surfactants, emulsifiers, wetting agents, thickeners or conditioners.

7. A composition according to claim 1 in a ready-to-use form.

8. A composition according to claim 1 further containing isoamyl laurate.

* * * * *